United States Patent [19]

Antos

[11] 4,025,418

[45] * May 24, 1977

[54] HYDROCARBON CONVERSION WITH AN ACIDIC SULFUR-FREE MULTIMETALLIC CATALYTIC COMPOSITE

[75] Inventor: George J. Antos, Arlington Heights, Ill.

[73] Assignee: UOP Inc., Des Plaines, Ill.

[ * ] Notice: The portion of the term of this patent subsequent to Feb. 17, 1993, has been disclaimed.

[22] Filed: Feb. 10, 1976

[21] Appl. No.: 656,925

Related U.S. Application Data

[63] Continuation-in-part of Ser. No. 550,083, Feb. 14, 1975, Pat. No. 3,939,059.

[52] U.S. Cl. .............................. 208/139; 208/111; 252/441; 260/673.5; 260/683.3; 260/683.68
[51] Int. Cl.$^2$ ................... C10G 35/08; B01J 27/06
[58] Field of Search ................ 208/111, 139; 260/673.5, 683.3, 683.68; 252/441, 466 PT

[56] References Cited

UNITED STATES PATENTS 3,939,059  2/1976  Antos ............................. 208/139

*Primary Examiner*—C. Davis
*Attorney, Agent, or Firm*—James R. Hoatson, Jr.; Thomas K. McBride; William H. Page, II

[57] ABSTRACT

Hydrocarbons are converted by contacting them at hydrocarbon conversion conditions with an acidic sulfur-free multimetallic catalytic composite comprising a combination of catalytically effective amounts of a platinum group component, a rhenium component, a cobalt component, and a halogen component with a porous carrier material. The platinum group component, rhenium component, cobalt component, and halogen component are present in the multimetallic catalyst in amounts respectively, calculated on an elemental basis, corresponding to about 0.01 to about 2 wt. % platinum group metal, about 0.01 to about 2 wt. % rhenium, about 0.1 to about 5 wt. % cobalt, and about 0.1 to about 3.5 wt. % halogen. Moreover, the catalytically active sites induced by these metallic components are uniformly dispersed throughout the porous carrier material and these components are present in the catalyst in carefully controlled oxidation states such that substantially all of the platinum group component is in the elemental metallic state, substantially all of the rhenium and catalytically available cobalt components are in the elemental metallic state or in a state which is reducible to the elemental metallic state under hydrocarbon conversion conditions, or in a mixture of these states. A specific example of the type of hydrocarbon conversion process disclosed is a process for the catalytic reforming of a low-octane gasoline fraction wherein the gasoline fraction and a hydrogen stream are contacted with the acidic sulfur-free multimetallic catalyst disclosed herein at reforming conditions.

26 Claims, No Drawings

HYDROCARBON CONVERSION WITH AN ACIDIC SULFUR-FREE MULTIMETALLIC CATALYTIC COMPOSITE

CROSS-REFERENCE TO RELATED APPLICATIONS

This application is a continuation-in-part of my prior, copending application Ser. No. 550,083 filed Feb. 14, 1975, now U.S. Pat. No. 3,939,059. All of the teachings of this prior application are specifically incorporated herein by reference.

The subject of the present invention is a novel acidic sulfur-free multimetallic catalytic composite which has exceptional activity and resistance to deactivation when employed in a hydrocarbon conversion process that requires a catalyst having both a hydrogenation-dehydrogenation function and a carbonium ion-forming function. More precisely, the present invention involves a novel dual-function acidic sulfur-free multimetallic catalytic composite which, quite surprisingly, enables substantial improvements in hydrocarbon conversion processes that have traditionally used a dual-function catalyst. In another aspect, the present invention comprehends the improved processes that are produced by the use of an acidic sulfur-free catalytic composite comprising a combination of catalytically effective amounts of a platinum group component, a cobalt component, a rhenium component, and a halogen component with a porous carrier material; specifically, an improved reforming process which utilizes the subject catalyst to improve activity, selectivity, and stability characteristics.

Composites having a hydrogenation-dehydrogenation function and a carbonium ion-forming function are widely used today as catalysts in many industries, such as the petroleum and petrochemical industry, to accelerate a wide spectrum of hydrocarbon conversion reactions. Generally, the carbonium ion-forming function is thought to be associated with an acid-acting material of the porous, adsorptive, refractory oxide type which is typically utilized as the support or carrier for a heavy metal component such as the metals or compounds of metals of Groups V through VIII of the Periodic Table to which are generally attributed the hydrogenation-dehydrogenation function.

These catalytic composites are used to accelerate a wide variety of hydrocarbon conversion reactions such as hydrocracking, hydrogenolysis, isomerization, dehydrogenation, hydrogenation, desulfurization, cyclization, polymerization, alkylation, cracking, hydroisomerization, dealkylation, transalkylation, etc. In many cases, the commercial applications of these catalysts are in processes where more than one of the reactions are proceeding simultaneously. An example of this type of process is reforming wherein a hydrocarbon feed-stream containing paraffins and naphthenes is subjected to conditions which promote dehydrogenation of naphthenes to aromatics, dehydrocyclization of paraffins to aromatics, isomerization of paraffins and naphthenes, hydrocracking and hydrogenolysis of naphthenes and paraffins, and the like reactions, to produce an octane-rich or aromatic-rich product stream. Another example is a hydrocracking wherein catalysts of this type are utilized to effect selective hydrogenation and cracking of high molecular weight unsaturated materials, selective hydrocracking of high molecular weight materials, and other like reactions, to produce a generally lower boiling, more valuable output stream. Yet another example is a hydroisomerization process wherein a hydrocarbon fraction which is relatively rich in straight-chain paraffin compounds is contacted with a dual-function catalyst to produce an output stream rich in isoparaffin compounds.

Regardless of the reaction involved or the particular process involved, it is of critical importance that the dual-function catalyst exhibit not only the capability to initially perform its specified functions, but also that it has the capability to perform them satisfactorily for prolonged periods of time. The analytical terms used in the art to measure how well a particular catalyst performs its intended functions in a particular hydrocarbon reaction environment are activity, selectivity, and stability. And for purposes of discussion here, these terms are conveniently defined for a given charge stock as follows: (1) activity is a measure of the catalyst's ability to convert hydrocarbon reactants into products at a specified severity level where severity level means the conditions used — that is, the temperature, pressure, contact time, and presence of diluents such as $H_2$; (2) selectivity refers to the amount of desired product or products obtained relative to the amount of reactants charged or converted; (3) stability refers to the rate of change with time of the activity and selectivity parameters — obviously, the smaller rate implying the more stable catalyst. In a reforming process, for example, activity commonly refers to the amount of conversion that takes place for a given charge stock at a specified severity level and is typically measured by octane number of the $C_5+$ product stream; selectivity refers to the amount of $C_5+$ yield, relative to the amount of the charge, that is obtained at the particular activity or severity level; and stability is typically equated to the rate of change with time of activity, as measured by octane number of $C_5+$ product and of selectivity as measured by $C_5+$ yield. Actually, the last statement is not strictly correct because generally a continuous reforming process is run to produce a constant octane $C_5+$ product with severity level being continuously adjusted to attain this result; and furthermore, the severity level is for this process usually varied by adjusting the conversion temperature in the reaction so that, in point of fact, the rate of change of activity finds response in the rate of change of conversion temperatures and changes in this last parameter are customarily taken as indicative of activity stability.

As is well known to those skilled in the art, the principal cause of observed deactivation or instability of a dual-function catalyst when it is used in a hydrocarbon conversion reaction is associated with the fact that coke forms on the surface of the catalyst during the course of the reaction. More specifically, in these hydrocarbon conversion processes, the conditions utilized typically result in the formation of heavy, high molecular weight, black, solid or semi-solid, carbonaceous material which is a hydrogen-deficient polymeric substance having properties akin to both polynuclear aromatics and graphite. This material coats the surface of the catalyst and thus reduces its activity by shielding its active sites from the reactants. In other words, the performance of this dual-function catalyst is sensitive to the presence of carbonaceous deposits or coke on the surface of the catalyst. Accordingly, the major problem facing workers in this area of the art is the development of more active and/or selective catalytic composites that are not as sensitive to the presence of these carbonaceous materials and/or have the capability to suppress the rate of the formation of these carbonaceous materials on the catalyst. Viewed in terms of performance parameters, the problem is to develop a dual-function catalyst having superior activity, selectivity, and stability characteristics. In particular, for a reforming process the problem is typically expressed in terms of shifting and stabilizing the $C_5+$ yield-octane relationship at the lowest possible severity level — $C_5+$ yield being representative of selectivity and octane being proportional to activity.

I have now found a dual-function acidic sulfur-free multimetallic catalytic composite which possesses improved activity, selectivity, and stability characteristics when it is employed in a process for the conversion of hydrocarbons of the type which have heretofore utilized dual-function acidic catalytic composites such as processes for isomerization, hydroisomerization, dehydrogenation, desulfurization, denitrogenization, hydrogenation, alkylation, dealkylation, disproportionation, polymerization, hydrodealkylation, transalkylation, cyclization, dehydrocyclization, cracking, hydrocracking, halogenation, reforming, and the like processes. In particular, I have ascertained that an acidic sulfur-free catalyst, comprising a combination of catalytically effective amounts of a platinum group component, a cobalt component, a rhenium component, and a halogen component with a porous carrier material, can enable the performance of hydrocarbon conversion processes utilizing dual-function catalysts to be substantially improved if the catalytically active sites induced by the metallic components are uniformly dispersed throughout the carrier material and if the oxidation states of the active metallic ingredients are controlled to be in the states hereinafter specified. Moreover, I have determined that an acidic sulfur-free catalytic composite, comprising a combination of catalytically effective amounts of a platinum group component, a rhenium component, a cobalt component, and a chloride component with an alumina carrier material, can be utilized to substantially improve the performance of a reforming process which operates on a low-octane gasoline fraction to produce a high-octane reformate if the catalytically active sites induced by the metallic components are uniformly dispersed throughout the alumina carrier material, if the catalyst is prepared and maintained during use in the process in a substantially sulfur-free state, and if the oxidation states of the catalytically available metallic components are fixed in the state hereinafter specified. In the case of a reforming process, the principal advantage associated with the use of the present invention involves the acquisition of the capability to operate in a stable manner in a high severity operation: for example, a low or moderate pressure reforming process designed to produce a $C_5+$ reformate having an octane of about 100 F-1 clear. As indicated, the present invention essentially involves the finding that the addition of a combination of a rhenium component and a cobalt component to a dual-function acidic hydrocarbon conversion catalyst containing a platinum group component can enable the performance characteristics of the catalyst to be sharply and materially improved, if the hereinafter specified limitations on amounts of ingredients, exclusion of sulfur, oxidation states of catalytically available metals, and distribution of catalytically active metallic components in the support are met.

It is, accordingly, one object of the present invention to provide an acidic sulfur-free multimetallic hydrocarbon conversion catalyst having superior performance characteristics when utilized in a hydrocarbon conversion process. A second object is to provide an acidic sulfur-free multimetallic catalyst having dual-function hydrocarbon conversion performance characteristics that are relatively insensitive to the deposition of hydrocarbonaceous material thereon. A third object is to provide preferred methods of preparation of this acidic sulfur-free multimetallic catalytic composite which insures the achievement and maintenance of its properties. Another object is to provide an improved reforming catalyst having superior activity, selectivity, and stability characteristics. Yet another object is to provide a dual-function hydrocarbon conversion catalyst which utilizes a combination of a rhenium component and a cobalt component to beneficially interact with and promote an acidic sulfur-free catalyst containing a platinum group component.

In brief summary, the present invention is, in one embodiment, an acidic sulfur-free catalytic composite comprising a porous carrier material containing, on an elemental basis, about 0.01 to about 2 wt. % platinum group metal, about 0.1 to about 5 wt. % cobalt, about 0.01 to about 2 wt. % rhenium, and about 0.1 to about 3.5 wt. % halogen; wherein the platinum group metal, rhenium and catalytically available cobalt are uniformly dispersed throughout the porous carrier material; wherein substantially all of the platinum group metal is present in the elemental metallic state; and wherein substantially all of the rhenium and catalytically available cobalt are present in the elemental metallic state or in a state which is reducible to the elemental metallic state under hydrocarbon conversion conditions or in a mixture of these states.

A second embodiment relates to an acidic sulfur-free catalytic composite comprising a porous carrier material containing, on an elemental basis, about 0.05 to about 1 wt. % platinum group metal, about 0.25 to about 2.5 wt. % cobalt, about 0.05 to about 1 wt. % rhenium, and about 0.5 to about 1.5 wt. % halogen; wherein the platinum group metal, rhenium, and catalytically available cobalt are uniformly dispersed throughout the porous carrier material; wherein substantially all of the platinum group metal is present in the corresponding elemental metallic state and wherein substantially all of the rhenium and catalytically available cobalt are present in the elemental metallic state or in a state which is reducible to the elemental metallic state under hydrocarbon conversion conditions or in a mixture of these states.

A third embodiment relates to the acidic catalytic composite described in the first or second embodiment wherein the halogen is combined chloride.

Yet another embodiment involves a process for the conversion of a hydrocarbon comprising contacting the hydrocarbon and hydrogen with the acidic catalytic composite described above in the first or second or third embodiment at hydrocarbon conversion conditions.

A preferred embodiment comprehends a process for reforming a gasoline fraction which comprises contacting the gasoline fraction and hydrogen with the acidic catalytic composite described above in the first or second or third embodiment at reforming conditions selected to produce a high octane reformate.

A highly preferred embodiment is a process for reforming a gasoline fraction which comprises contacting the gasoline fraction and hydrogen in a substantially water-free and sulfur-free environment with the acidic catalytic composite characterized in the first, second, or third embodiment at reforming conditions selected to produce a high octane reformate.

Other objects and embodiments of the present invention related to additional details regarding essential, preferred and optional catalytic ingredients, preferred amounts of ingredients, suitable methods of composite preparation, operating conditions for use in the hydrocarbon conversion processes, and the like particulars. These are hereinafter given in the following detailed discussion of each of these facets of the present invention.

The acidic multimetallic catalyst of the present invention comprises a porous carrier material or support having combined therewith catalytically effective amounts of a platinum group component, a cobalt component, a rhenium component, and a halogen component.

Considering first the porous carrier material utilized in the present invention, it is preferred that the material be a porous, adsorptive, high surface area support having a surface area of about 25 to about 500 $m^2/g$. The porous carrier material should be relatively refractory to the conditions utilized in the hydrocarbon conversion process, and it is intended to include within the scope of the present invention carrier materials which have traditionally been utilized in dual-function hydrocarbon conversion catalysts such as: (1) activated carbon, coke, or charcoal; (2) silica or silica gel, silicon carbide, clays, and silicates including those synthetically prepared and naturally occurring, which may or may not be acid treated for example, attapulgus clay, china clay, diatomaceous earth, fuller's earth, kaolin, kieselguhr, etc. (3) ceramics, porcelain, crushed firebrick, bauxite; (4) refractory inorganic oxides such as alumina, titanium dioxide, zirconium dioxide, chromium oxide, beryllium oxide, vanadium oxide, cesium oxide, hafnium oxide, zinc oxide, magnesia, boria, thoria, silica-alumina, silica-magnesia, chromia-alumina, alumina-boria, silica-zirconia, etc.; (5) crystalline zeolitic aluminosilicates such as naturally occurring or synthetically prepared mordenite and/or faujasite, either in the hydrogen form or in a form which has been treated with multivalent cations; (6) spinels such as $MgAl_2O_4$, $FeAl_2O_4$, $ZnAl_2O_4$, $MnAl_2O_4$, $CaAl_2O_4$, and other like compounds having the formula $MO.Al_2O_3$ where M is a metal having a valence of 2; and (7) combinations of elements from one or more of these groups. The preferred porous carrier materials for use in the present invention are refractory inorganic oxides, with best results obtained with an alumina carrier material. Suitable alumina materials are the crystalline aluminas known as gamma-, eta-, and theta-alumina, with gamma- or eta-alumina giving best results. In addition, in some embodiments the alumina carrier material may contain minor proportions of other well known refractory inorganic oxides such as silica, zirconia, magnesia, etc.; however, the preferred support is substantially pure gamma- or eta-alumina. Preferred carrier materials have an apparent bulk density of about 0.3 to about 0.8 g/cc and surface area characteristics such that the average pore diameter is about 20 to 300 Angstroms, the pore volume is about 0.1 to about 1 cc/g and the surface area is about 100 to about 500 $m^2/g$. In general, best results are typically obtained with a gamma-alumina carrier material which is used in the form of spherical particles having: a relatively small diameter (i.e. typically about 1/16 inch), an apparent bulk density of about 0.3 to about 0.8 g/cc, a pore volume of about 0.4 ml/g, and a surface area of about 150 to about 250 $m^2/g$.

The preferred alumina carrier material may be prepared in any suitable manner and may be synthetically prepared or natural occurring. Whatever type of alumina is employed, it may be activated prior to use by one or more treatments including drying, calcination, steaming, etc., and it may be in a form known as activated alumina, activated alumina of commerce, porous alumina, alumina gel, etc. For example, the alumina carrier may be prepared by adding a suitable alkaline reagent, such as ammonium hydroxide, to a salt of aluminum such as aluminum chloride, aluminum nitrate, etc., in an amount to form an aluminum hydroxide gel which upon drying and calcining is converted to alumina. The alumina carrier may be formed in any desired shape such as spheres, pills, cakes, extrudates, powders, granules, tablets, etc., and utilized in any desired size. For the purpose of the present invention a particularly preferred form of alumina is the sphere, and alumina spheres may be continuously manufactured by the well known oil drop method which comprises: forming an alumina hydrosol by any of the techniques taught in the art and preferably by reacting aluminum metal with hydrochloric acid, combining the resultant hydrosol with a suitable gelling agent and dropping the resultant mixture into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 300° F. to about 400° F. and subjected to a calcination procedure at a temperature of about 850° F. to about 1300° F. for a period of about 1 to about 20 hours. This treatment effects conversion of the alumina hydrogel to the corresponding crystalline gamma-alumina. See the teachings of U.S. Pat. No. 2,620,314 for additional details.

As used herein, the expression "catalytically available cobalt" is intended to mean the portion of the cobalt component of the subject catalytic composite that is available for use in accelerating the particular hydrocarbon conversion reaction of interest. For purposes of the present invention, it is highly preferred that the catalytically available cobalt comprise at least about 10% of the total cobalt content of the catalyst and, even more preferably, at least about 50% or more thereof. For certain types of carrier materials which can be used in the preparation of the instant catalyst composite, it has been observed that a portion of the cobalt incorporated therein is essentially bound-up in the crystal structure thereof in a manner which essentially makes it catalytically unavailable; in fact it is more a part of the refractory carrier material than a catalytically active component. Specific examples of this effect are observed when the carrier material can form a refractory spinel or spinel-like structure with a portion of the cobalt component and/or when a refractory cobalt oxide or aluminate is formed by reactions of the carrier material (or precursors thereof) with a portion of the cobalt component. When this effect occurs, it is only with great difficulty that the portion of the cobalt bound-up with the support can be reduced to a catalytically active state and the conditions required to do this are beyond the severity levels normally associated with hydrocarbon conversion conditions and are in fact likely to seriously damage the necessary porous characteristics of the support. In the cases where cobalt can interact with the crystal structure of the support to render a portion thereof catalytically unavailable, the concept of the present invention merely requires that the amount of cobalt added to the subject catalyst be adjusted to satisfy the requirements of the support as well as the catalytically available or active cobalt requirements of the present invention. Against this background then, the hereinafter stated specifications for oxidation state and dispersion of the cobalt component are to be interpreted as directed to a description of the catalytically available cobalt. On the other hand, the specifications for the amount of cobalt used are to be interpreted to include all of the cobalt contained in the catalyst in any form.

One essential ingredient of the present catalytic composite is a rhenium component. It is of fundamental importance that substantially all of the rhenium component exists within the catalytic composite of the present invention in the elemental metallic state or in a state which is reducible to the elemental metallic state under hydrocarbon conversion conditions or in a mixture of these states. The rhenium component may be utilized in the composite in any amount which is catalytically effective, with the preferred amount being about 0.01 to about 2 wt. % thereof, calculated on an elemental basis. Typically, best results are obtained with about 0.05 to about 1 wt. % rhenium. It is additionally preferred to select the specified amount of rhenium from within this broad weight range as a function of the amount of the platinum group component, on an atomic basis, as is explained hereinafter.

This rhenium component may be incorporated into the catalytic composite in any suitable manner known to those skilled in the catalyst formulation art which results in a relatively uniform distribution of rhenium in the carrier material such as by coprecipitation, ion-exchange, or impregnation. In addition, it may be added at any stage of the preparation of the composite — either during preparation of the carrier material or thereafter — and the precise method of incorporation used is not deemed to be critical. However, best results are obtained when the rhenium component is relatively uniformly distributed throughout the carrier material in a relatively small particle size, and the preferred procedures are the ones known to result in a composite having this relatively uniform distribution. One acceptable procedure for incorporating this component into the composite involves cogelling or coprecipitating the rhenium component during the preparation of the preferred carrier material, alumina. This procedure usually comprehends the addition of a soluble, decomposable compound of rhenium such as perrhenic acid or a salt thereof to the alumina hydrosol before it is gelled. The resulting mixture is then finished by conventional gelling, aging, drying, and calcination steps as explained hereinbefore. A preferred way of incorporating this component is an impregnation step wherein the porous carrier material is impregnated with a suitable rhenium-containing solution either before, during, or after the carrier material is calcined. Preferred impregnation solutions are aqueous solutions of water soluble, decomposable rhenium compounds such as ammonium perrhenate, sodium perrhenate, potassium perrhenate, potassium rhenium oxychloride ($K_2ReOCl_5$), potassium hexachlororhenate (IV), rhenium chloride, rhenium heptoxide, and the like compounds. Best results are ordinarily obtained when the impregnation solution is an aqueous solution of perrhenic acid. This component can be added to the carrier material either prior to, simultaneously with, or after the other metallic components are combined therewith. Best results are usually achieved when this component is added simultaneously with the other metallic components. In fact, excellent results are obtained with a one step impregnation procedure using an acidic aqueous solution containing chloroplatinic acid, perrhenic acid, cobaltous chloride, and hydrochloric acid.

A second essential ingredient of the subject catalyst is the platinum group component. That is, it is intended to cover the use of platinum, iridium, osmium, ruthenium, rhodium, palladium, or mixtures thereof, as a second component of the present composite. It is an essential feature of the present invention that substantially all of this platinum group component exists within the final catalytic composite in the elemental metallic state. Generally, the amount of this component present in the final catalytic composite is small compared to the quantities of the other components combined therewith. In fact, the platinum group generally will comprise about 0.01 to about 2 wt. % of the final catalyti composite, calculated on an elemental basis. Excellent results are obtained when the catalyst contains about 0.05 to about 1 wt. % of platinum, iridium, rhodium, or palladium metal. Particularly preferred mixtures of these metals are platinum and iridium, and platinum and rhodium.

This platinum group component may be incorporated in the catalytic composite in any suitable manner known to result in a relatively uniform distribution of this component in the carrier material such as coprecipitation or cogelation, ion-exchange or impregnation. The preferred method of preparing the catalyst involves the utilization of a soluble, decomposable compound of platinum group metal to impregnate the carrier material in a relatively uniform manner. For example, this component may be added to the support by commingling the latter with an aqueous solution of chloroplatinic or chloroiridic or chloropalladic acid. Other water-soluble compounds or complexes of platinum group metals may be employed in impregnation solutions and include ammonium chloroplatinate, bromoplatinic acid, platinum trichloride, platinum tetrachloride hydrate, platinum dichlorocarbonyl dichloride, dinitrodiaminoplatinum, sodium tetranitroplatinate (II), palladium chloride, palladium nitrate, palladium sulfate, diamminepalladium (II) hydroxide, tetramminepalladium (II) chloride, hexamminerhodium chloride, rhodium carbonylchloride, rhodium trichloride hydrate, rhodium nitrate, sodium hexachlororhodate (III), sodium hexanitrorhodate (III), iridium tribromide, iridium dichloride, iridium tetrachloride, sodium hexanitroiridate (III), potassium or sodium chloroiridate, potassium rhodium oxalate, etc. The utilization of a platinum, iridium, rhodium or palladium chloride compound, such as chloroplatinic, chloroiridic, or chloropalladic acid or rhodium trichloride hydrate, is preferred since it facilitates the incorporation of both the platinum group components and at least a minor quantity of the halogen component in a single step. Hydrogen chloride or the like acid is also generally added to the impregnation solution in order to further facilitate the incorporation of the halogen component and the uniform distribution of the metallic components throughout the carrier material. In addition, it is generally preferred to impregnate the carrier material after it has been calcined in order to minimize the risk of washing away the valuable platinum or palladium compounds; however, in some cases, it may be advantageous to impregnate the carrier material when it is in a gelled state.

A third essential ingredient of the acidic sulfur-free multimetallic catalytic composite of the present invention is a cobalt component. Although this component may be initially incorporated into the composite in many different decomposable forms which are hereinafter stated, my basic finding is that the catalytically active state for hydrocarbon conversion with this component is the elemental metallic state. Consequently, it is a feature of my invention that substantially all of the catalytically available cobalt component exists in the catalytic composite either in the elemental metallic state or in a state which is reducible to the elemental state under hydrocarbon conversion conditions or in a mixture of these states. Examples of the reducible state are obtained when the catalytically available cobalt component is initially present in the form of cobalt oxide, hydroxide, halide, oxyhalide, and the like reducible compounds. As a corollary to this basic finding on the active state of the catalytically available cobalt component, it follows that the presence of the catalytically available cobalt in forms which are not reducible at hydrocarbon conversion conditions is to be scrupulously avoided if the full benefits of the present invention are to be realized. Illustrative of these undesired forms are cobalt sulfide and the cobalt oxysulfur compounds such as cobalt sulfate. Best results are obtained when the composite initially contains substantially all of the catalytically available cobalt component in the elemental metallic state or in a reducible oxide state or in a mixture of these states. All available evidence indicates that the preferred impregnation procedure hereinafter results in a catalyst having the catalytically available cobalt component in a reducible oxide form. Based on the performance of such a catalyst, it is believed that substantially all of this reducible oxide form of the cobalt component is reduced to the elemental metallic state when a hydrocarbon conversion process (such as reforming) using this catalyst is started-up and lined-out at hydrocarbon conversion conditions. The cobalt component may be utilized in the composite in any amount which is catalytically effective, with the preferred amount being about 0.1 to about 5 wt. % thereof, calculated on an elemental cobalt basis. Typically, best results are obtained with about 0.25 to about 2.5 wt. % cobalt. It is, additionally, preferred to select the specific amount of cobalt from within this broad weight range as a function of the amount of the platinum group component, on an atomic basis, as is explained hereinafter.

The cobalt component may be incorporated into the catalytic composite in any suitable manner known to those skilled in the catalyst formulation art to result in a relatively uniform distribution of the catalytically available cobalt in the carrier material such as coprecipitation, cogelation, ion-exchange, impregnation, etc. In addition, it may be added at any stage of the preparation of the composite — either during preparation of the carrier material or thereafter — since the precise method of incorporation used is not deemed to be critical. However, best results are obtained when the catalytically available cobalt component is relatively uniformly distributed throughout the carrier material in a relatively small particle or crystallite size having a maximum dimension of less than 100 Angstroms, and the preferred procedures are the ones that are known to result in a composite having a relatively uniform distribution of the catalytically available cobalt moiety in a relatively small particle size. One acceptable procedure for incorporating this component into the composite involves cogelling or coprecipitating the cobalt component during the preparation of the preferred carrier material, alumina. This procedure usually comprehends the addition of a soluble, decomposable, and reducible compound of cobalt such as cobalt chloride or nitrate to the alumina hydrosol before it is gelled. Alternatively, the reducible compound of cobalt can be added to the gelling agent before it is added to the hydrosol. The resulting mixture is then finished by conventional gelling, aging, drying, and calcination steps as explained hereinbefore. One preferred way of incorporating this component is an impregnation step wherein the porous carrier material is impregnated with a suitable cobalt-containing solution either before, during, or after the carrier material is calcined or oxidized. The solvent used to form the impregnation solution may be water, alcohol, ether, or any other suitable organic or inorganic solvent provided the solvent does not adversely interact with any of the other ingredients of the composite or interfere with the distribution and reduction of the cobalt component. Preferred impregnation solutions are aqueous solutions of water-soluble, decomposable, and reducible cobalt compounds such as cobaltous acetate, cobaltous benzoate, cobaltous bromate, cobaltous bromide, cobaltous chlorate and perchlorate, cobaltous chloride, cobaltic chloride, cobaltous fluoride, cobaltous iodide, cobaltous nitrate, hexamminecobalt (III) chloride, hexamminecobalt (III) nitrate, triethylenediamminecobalt (III) chloride, cobaltous hexamethylenetriamine, and the like compounds. Best results are ordinarily obtained when the impregnation solution is an aqueous solution of cobalt chloride, acetate or nitrate. This cobalt component can be added to the carrier material, either prior to, simultaneously with, or after the other metallic components are combined therewith. Best results are usually achieved when this component is added simultaneously with the platinum group and rhenium components via an acidic aqueous impregnation solution. In fact, excellent results are obtained with an impregnation procedure using an acidic aqueous solution comprising chloroplatinic acid, perrhenic acid, cobaltous chloride, and hydrochloric acid.

It is essential to incorporate a halogen component into the acidic sulfur-free multimetallic catalytic composite of the present invention. Although the precise form of the chemistry of the association of the halogen component with the carrier material is not entirely known, it is customary in the art to refer to the halogen component as being combined with the carrier material, or with the other ingredients of the catalyst in the form of the halide (e.g. as the chloride). This combined halogen may be either fluorine, chlorine, iodine, bromine, or mixtures thereof. Of these, fluorine and, particularly, chlorine are preferred for the purposes of the present invention. The halogen may be added to the carrier material in any suitable manner, either during preparation of the support or before or after the addition of the other components. For example, the halogen may be added, at any stage of the preparation of the carrier material or to the calcined carrier material, as an aqueous solution of a suitable, decomposable halogen-containing compound such as hydrogen fluoride, hydrogen chloride, hydrogen bromide, ammonium chloride, etc. The halogen component or a portion thereof, may be combined with the carrier material during the impregnation of the latter with the platinum group, cobalt, or rhenium components; for example, through the utilization of a mixture of chloroplatinic acid and hydrogen chloride. In another situation, the alumina hydrosol which is typically utilized to form the preferred alumina carrier material may contain halogen and thus contribute at least a portion of the halogen component to the final composite. For reforming, the halogen will be typically combined with the carrier material in an amount sufficient to result in a final composite that contains about 0.1 to about 3.5%, and preferably about 0.5 to about 1.5%, by weight of halogen, calculated on an elemental basis. In isomerization or hydrocracking embodiments, it is generally preferred to utilize relatively larger amounts of halogen in the catalyst — typically, ranging up to about 10 wt. % halogen calculated on an elemental basis, and more preferably, about 1 to about 5 wt. %. It is to be understood that the specified level of halogen component in the instant catalyst can be achieved or maintained during use in the conversion of hydrocarbons by continuously or periodically adding to the reaction zone a decomposable halogen-containing compound such as an organic chloride (e.g. ethylene dichloride, carbon tetrachloride, t-butyl chloride) in an amount of about 1 to 100 wt. ppm. of the hydrocarbon feed, and preferably about 1 to 10 wt. ppm.

Regarding especially preferred amounts of the various metallic components of the subject catalyst, I have found it to be an excellent practice to specify the amount of the cobalt component and the rhenium component as a function of the amount of the platinum group component. On this basis, the amount of the cobalt component is ordinarily selected so that the atomic ratio of cobalt to platinum group metal contained in the composite is about 0.2:1 to about 66:1, with the preferred range being about 0.8:1 to about 18:1. Similarly, the amount of the rhenium component is ordinarily selected to produce a composite containing an atomic ratio of rhenium to platinum group metal of about 0.05:1 to about 10:1, with the preferred range being about 0.2:1 to about 5:1.

Another significant parameter for the instant catalyst is the "total metals content" which is defined to be the sum of the platinum group component, the cobalt component, and the rhenium component, calculated on an elemental basis. Good results are ordinarily obtained with the subject catalyst when this parameter is fixed at a value of about 0.15 to about 4 wt.%, with best results ordinarily achieved at a metals loading of about 0.3 to about 3 wt.%.

In embodiments of the present invention wherein the instant multimetallic catalytic composite is used for the dehydrogenation of dehydrogenatable hydrocarbons or for the hydrogenation of hydrogenatable hydrocarbons, it is ordinarily a preferred practice to include an alkali or alkaline earth metal componet in the composite and to minimize or eliminate the halogen component. More precisely, this optional ingredient is selected from the group consisting of the compounds of the alkali metals — cesium, rubidium, potassium, sodium, and lithium — and the compounds of the alkaline earth metals — calcium, strontium, barium, and magnesium. Generally good results are obtained in these embodiments when this component constitutes about 0.1 to about 5 wt.% of the composite, calculated on an elemental basis. This optional alkali or alkaline earth metal componet can be incorporated in the composite in any of the known ways, with impregnation with an aqueous solution of a suitable water-soluble, decomposable compound being preferred.

An optional ingredient for the multimetallic catalyst of the present invention is a Friedel-Crafts metal halide component. This ingredient is particularly useful in hydrocarbon conversion embodiments of the present invention wherein it is preferred that the catalyst utilized has a strong acid or cracking function associated therewith — for example, an embodiment wherein hydrocarbons are to be hydrocracked or isomerized with the catalyst of the present invention. Suitable metal halides of the Friedel-Crafts type include aluminum chloride, aluminum bromide, ferric chloride, ferric bromide, zinc chloride, and the like compounds, with the aluminum halides and particularly aluminum chloride ordinarily yielding best results. Generally, this optional ingredient can be incorporated into the composite of the present invention by any of the conventional methods for adding metallic halides of this type; however, best results are ordinarily obtained when the metallic halide is sublimed onto the surface of the carrier material according to the preferred method disclosed in U.S. Pat. No. 2,999,074. The component can generally be utilized in any amount which is catalytically effective, with a vale selected from the range of about 1 to about 100 wt% of the carrier material generally being preferred.

Regardless of the details of how the components of the catalyst are combined with the porous carrier material, the final catalyst generally will be dried at a temperature of about 200° to about 600° F. for a period of at least about 2 to about 24 hours or more, and finally calcined or oxidized at a temperature of about 700° F. to about 1100° F. in an air to oxygen atmosphere for a period of about 0.5 to about 10 hours in order to convert substantially all of the metallic components to the corresponding oxide form. Because a halogen component is utilized in the catalyst, best results are generally obtained when the halogen content of the catalyst is adjusted during the oxidation step by including a halogen or a halogen-containing compound such as HCl or an HCl-producing substance in the air or oxygen atmosphere utilized. In particular, when the halogen component of the catalyst is chlorine, it is preferred to use a mole ratio of $H_2O$ to HCl of about 5:1 to about 100:1 during at least a portion of the oxidation step in order to adjust the final chlorine content of the catalyst to a range of about 0.1 to about 3.5 wt.%. Preferably, the duration of this halogenation step if about 1 to 5 hours.

The resultant oxidized catalytic composite is preferably subjected to a substantially water-free and hydrocarbon-free reduction step prior to its use in the conversion of hydrocarbons. This step is designed to selectively reduce at least the platinum group component to the element metallic state and to insure a uniform and d finely divided dispersion of the metallic components throughout the carrier material. Preferably substantially pure and dry hydrogen (i.e. less than 20 vol. ppm. $H_2O$) is used as the reducing agent in this step. The reducing agent is contacted with the oxidized catalyst at conditions including a reduction temperature of about 800° F. to about 1200° F. and a period of time of about 0.5 to 10 hours effective to at least reduce substantially all of the platinum group component to the elemental metallic state. Quite surprisingly, it has been found that if this reduction step is performed with a hydrocarbon-free hydrogen stream at the temperature indicated, and if the catalytically available cobalt component is properly distributed in the carrier material in the oxide form and in the specified particle size, no substantial amount of the catalytically available cobalt component will be reduced in this step. However, once the catalyst sees a mixture of hydrogen and hydrocarbon at least a major portion of the catalytically available cobalt component is quickly reduced at the specified reduction temperature range. More precisely, after a hydrocarbon conversion process using the instant catalyst is started-up and lined-out at hydrocarbon conversion condition, it is believed that substantially all of the catalytically available cobalt is present in the elemental metallic state. This reduction treatment may be performed in situ as part of a start-up sequence if precautions are taken to predry the plant to a substantially water-free state and if substantially water-free and hydrocarbon-free hydrogen is used.

The resulting reduced catalystic composite is, in accordance with the basic concept of the present invention, preferably maintained in a sulfur-free state both during its preparation and thereafter during its use in the conversion of hydrocarbons. As indicated previously, the beneficial interaction of the catalytically available cobalt component with the the other ingredient of the present catalytic composite is contingent upon the maintenance of the cobalt moiety in a highly dispersed, readily reducible state in the carrier material. Sulfur in the form of a sulfide adversely interferes with both the dispersion and reducibility of the catalytically available cobalt component and consequently it is a highly preferred practice to avoid presulfiding the selectively reduced acidic multimetallic catalyst resulting from the reduction step. Once the catalyst has been exposed to hydrocarbon for a sufficient period of time to lay down a protective layer of carbon or coke on the surface thereof, the sulfur senstivity of the resulting carbon-containing composite changes rather markedly and the presence of small amounts of sulfur can be tolerated without permanently disabling the catalyst. The exposure of the freshly reduced catalyst to sulfur can seriously damage the cobalt component thereof and consequently, jeoparize the superior performance characteristics associated therewith. However, once a protective layer of carbon is established on the catalyst, the sulfur deactivation effect is less than permanent and sulfur can be purged therefrom by exposure to a sulfur-free hydrogen stream at a temperature of about 800° to 1100° F.

According to the present invention, a hydrocarbon charge stock and hydrogen are contacted with the instant acid sulfur-free multimetallic catalyst in a hydrocarbon converision zone. This contacting may be accomplished by using the catalyst in a fixed bed system, a moving bed system, a fluidized bed system, or in a batch type operation, however, in view of the danger of attrition losses of the valuable catalyst and of well-known operational advantages, it is preferred to use either a fixed bed system or a dense-phase moving bed system such as is shown in U.S. Pat. No. 3,725,249. It is also contemplated that the contacting step can be performed in the presence of a physical mixture of particles of the catalyst of the present invention and particles of a conventional dual-function catalyst of the prior art. In a fixed bed system, a hydrogen-rich gas and the charge stock are preheated by any suitable heating means to the desired reaction temperature and then are passed into a conversion zone containing a fixed bed of the acidic multimetallic catalyst. It is, of course, understood that the conversion zone may be one or more separate reactors with suitable means therebetween to insure that the desired conversion temperature is maintained at the entrance to each reactor. It is also important to note that the reactancts may be contacted with the catalyst bed in either upward, downward, or radial flow fashion with the latter being preferred. In addition, the reactants may be in the liquid phase, a mixed liquid-vapor phase, or a vapor phase when they contact the catalyst, with best results obtained in the vapor phase.

In the case where the acidic sulfur-free multimetallic catalyst of the present invention is used in a reforming operation, the reforming system will typically comprise a reforming zone containing one or more fixed beds or dense-phase moving beds of the catalysts. In a multiple bed system, it is, or course, within the scope of the present invention to use the present catalyst in less than all of the beds with a conventional dual-function catalyst being used in the remainder of the beds. This reforming zone may be one or more separate reactors with suitable heating means therebetween to compensate for the endothermic nature of the reactions that take place in each catalyst bed. The hydrocarbon feed stream that is charged to this reforming system will comprise hydrocarbon fractions containing naphthenes and paraffins that boil within the gasoline range. The preferred charge stocks are those consisting essentially of naphthenes and paraffins, although in some cases aromatics and/or olefins may also be present. This preferred class includes straight run gasolines, natural gasolines, synthetic gasolines, partially reformed gasolines, and the like. On the other hand, it is frequently advantageous to charge thermally or catalytically cracked gasolines or higher boiling fractions thereof. Mixtures of straight run and cracked gasolines can also be used to advantage. The gasoline charge stock may be a full boiling gasoline having an initial boiling point of from about 50° to about 150° F. and an end boiling point within the range of from about 325° to about 425° /F., or may be a selected fraction thereof which generally will be a higher boiling fraction commonly referred to as a heavy naphtha — for example, a naphtha boiling in the range of $C_7$ to 400° F. In some cases, it is also advantageous to charge pure hydrocarbons or mixtures of hydrocarbons that have been extracted from hydrocarbon distillates — for example, straight-chain paraffins — which are to be converted to aromatics. It is preferred that these charge stocks be treated by conventional catalytic pretreatment methods such as hydrorefining, hydrotreating, hydrodesulfurization, etc., to remove substantially all sulfurous, nitorgenous, and water-yielding contaminants therefrom and to saturate any olefins that may be contained therein.

In other hydrocarbon conversion embodiments, the charge stock will be of the conventional type customarily used for theparticular kind of hydrocarbon conversion being effected. For example, in a typical isomerization embodiment the charge stock can be a paraffinic stock rich in $C_4$ to $C_8$ normal paraffins, or a normal butane-rich stock or a n-hexane-rich stock, or a mixture of xylene isomers, or an olefin-containing stock, etc. In a dehydrogenation embodiment, the charge stock can be any of the known dehydrogenatable hydrocarbons such as an aliphatic compound containing 2 to 30 carbon atoms per molecule, a $C_4$ to $C_{30}$ normal paraffin, a $C_8$ to $C_{12}$ alkylaromztic, a naphthene, and the like. In hydrocracking embodiments, the charge stock will be typically a gas oil, heavy cracked cycle oil, etc. In addition, alkylaromatics, olefins, and naphthenes can be coveniently isomerized by using the catalyst of the present invention. Likewise, pure hydrocarbons or substantially pure hydrocarbons can be converted to more valuable products by using the acidic sulfur-free multimetallic catalyst of the present invention in any of the hydrocarbon conversion processes, known to the art, that use a dual-function catalyst.

Since sulfur has a high affinity for cobalt at hydrocarbon conversion conditions, I have found that best reaslts are achieved in the conversion of hydrocarbons with the instant acidic multimetallic catalytic composite when the catalyst is used in a substantially sulfur-free environment. This is particularly true in the catalytic reforming embodiment of the present invention. The expression "substantially sulfur-free environment" is intended to means that the total amount (expressed as equivalent elemental sulfur) of sulfur or sulfur-containing compounds, which are capable of producing a metallic sulfide at the reaction conditions used, entering the reaction zone containing the instant catalyst from any source is continuously maintained at an amount equivalent to less than 10 wt. ppm. of the hydrocarbon charge stock, more preferably less than 5 wt. ppm., and most preferably less than 1 wt. ppm. Since in the ordinary operation of a conventional catlytic reforming process, wherein influent hydrogen is autogeneously produced, the prime source for any sulfur entering the reforming zone is the hydrocarbon charge stock, maintaining the charge stock substantially free of sulfur is ordinarily sufficient to ensure that the environment containing the catalyst is maintained in the substantially sulfur-free state. More specifically, since hydrogen is a by-product of the catalytic reforming process, ordinarily the input hydrogen stream required for the process is obtained by recycling a portion of the hydrogen-rich stream recovered from the effluent withdrawn from the reforming zone. In this typical situation, this recycle hydrogen stream will ordinarily be substantially free of sulfur if the charge stock is maintained free of sulfur. If autogeneous hydrogen is not utilized, then, of course the concept of the present invention requires that the input hydrogen stream be maintained substantially sulfur-free; that is, less than 10 vol. ppm. of $H_2S$, preferably less than 5 vol. ppm., and most preferably less than 1 vol. ppm.

The only other possible sources of sulfur that could interfere with the performance of the instant catalyst are sulfur that is initially combined with the catalyst and/or with the plant hardwark. As indicated hereinbefore, a highly preferred feature of the present acidic multimetallic catalyst is that it is maintained in a substantially sulfur-free state; therefore, sulfur released from the catalyst is not usually a problem in the present process. Hardware sulfur is ordinarily not present in a new plant; it only becomes a problem when the present process is to be implemented in a plant that has been in service with a sulfur-containing feedstream. In this latter case, the preferred practice of the present invention involves an initial pretreatment of the sulfur-containing plant in order to remove substantially all of the decomposable hardware sulfur therefrom. This can be easily accomplished by any of the techniques for stripping sulfur from hardware known to those in the art; for example, by the circulation of a substantially sulfur-free hydrogen stream through the internals of the plant at a relatively high temperature of about 800° to about 1200' F. until the $H_2S$ content of the effluent gas stream drops to a relatively low level — typically, less than 5 vol. ppm. and preferably less than 2 vol. ppm. In sum, the sulfur-free feature of the present invention requires that the total amount of detrimental sulfur entering the hydrocarbon conversion zone containing the hereinbefore described acidic multimetallic catalyst must be continuously maintained at a substantially low level; specifically, the amount of sulfur must be held to a level equivalent to less than 10 wt. ppm., and preferably less than 1 wt. ppm., of the feed.

In the case where the sulfur content of the feed stream for the present process is greater than the amounts previously specified, it is, of course, necessary to treat the charge stock in order to remove the undesired sulfur contaminats therefrom. This is easily accomplished by using any one of the conventional catalytic pretreatment methods such as hydrorefining, hydrotreating, hydrodesulfurization, and the like to remove substantially all sulfurous, nitogenous, and water-yielding contaminants from this feedstream. Ordinarily, this involves subjecting the sulfur-containing feestream to contact with a suitable sulfur-resistant hydrorefining catalyst in the presence of hydrogen under conversion conditions selected to decompose sulfur contaminants contained therein and form hydrogen sulfide. The hydrorefining catalyst typically comprises one or more of the oxides or sulfides of the transition metals of Groups VI and VIII of the Periodic Table. A particularly preferred hydrorefining catalyst comprises a combination of a metallic component from the iron group metals of Group VIII and of a metallic component of the Group VI transition metals combined with a suitable porous refractory support. Particularly good results have been obtained when the group component is cobalt and/or nickel and the Group VI transition metal is molybdenum or tungsten. The preferred support for this type of catalyt is a refractory inorganic oxide of the type previously mentioned. For example, good results are obtained with a hydrorefining catalyst comprising cobalt oxide and molybdenum oxide supported on a carrier material comprising alumina and silica. The conditions utilized in this hydrorefining step are ordinarily selected from the following ranges: a temperature of about 600° to about 950° F., a pressure of about 500 to about 5000 psig., a liquid hourly space velocity of about 1 to about 20 hr.$^{-1}$, and a hydrogen circulation rate of about 500 to about 10,000 standard cubic feet of hydrogen per barrel of charge. After this hydrorefining step, the hydrogen sulfide, ammonia, and water liberated therein, are then easily removed from the resulting purified charge stock by conventional means such as a suitable stripping operation. Specific hydrorefining conditions are selected from the ranges given above as a function of the amounts and kinds of the sulfur contaminants in the feedstream in order to product a substantially sulfur-free charge stock which is then charged to the process of the present invention.

In a reforming embodiment, it is generally preferred to utilize the novel acidic sulfur-free multimetallic catalytic composite in a substantially water-free environment. Essential to the achievement of this condition in the reforming zone is the control of the water level present in the charge stock and the hydrogen stream which is being charged to the zone. Best results are ordinarily obtained when the total amount of water entering the conversion zone from any source is held to a level less than 20 ppm, and preferably less than 5 ppm. expressed as weight of equivalent water in the charge stock. In general, this can be accomplished by careful control of the water present in the charge stock and in the hydrogen stream. The charge stock can be dried by using any suitable drying means known to the art, such as a coventional solid adsorbent having a high selectivity for water, for instance, sodium or calcium crystalline aluminosilicates, silica gel, activated alumina, molecular sieves, anhydrous calcium sulfate, high surface area sodium, and the like adsorbents. Similarly, the water content of the charge stock may be adjusted by suitable stripping operations in a fractionation column or like device. And in some cases, a combination of adsorbent drying and distillation drying may be used advantageously to effect almost complete removal of water from the charge stock. In an especially preferred mode of operation, the charge stock is dried to a level corresponding to less than 5 wt. ppm. of $H_2O$ equivalent. In general, it is preferred to maintain the hydrogen stream entering the hydrocarbon conversion zone at a level of about 10 vol. ppm. of water or less and most preferably about 5 vol. ppm. or less. If the water level in the hydrogen stream is too high, drying of same can be coveniently accomplished by contacting the hydrogen stream with a suitable desiccant such as those mentioned above.

In the reforming embodiment, an effluent stream is withdrawn from the reforming zone and passed through a cooling means to a separation zone, typically at about 25° to 150° F., wherein a hydrogen-rich gas stream is separated from a high octane liquid product stream, commonly called an unstabilized reformate. When the water level in the hydrogen stream is outside the range previously specified, at least a portion of this hydrogen-rich gas stream is withdrawn from the separating zone and passed through an adsorption zone containing an adsorbent selective for water. The resultant substantially water-free hydrogen stream can then be recycled through suitable compressing means back to the reforming zone. The liquid phase from the separating zone is typically withdrawn and commonly treated in a fractionating system in order to adjust the butane concentration, thereby controlling front-end volatility of the resulting reformate.

The operating conditions utilized in the numerous hydrocarbon conversion embodiments of the present invention are in general those customarily used in the art for the particular reaction, or combination of reactions, that is to be effected. For instance, alkylaromatic, olefin, and paraffin isomerization conditions include: a temperature of about 32° F. to about 1000° F. and preferably from about 75' to about 600° F., a pressure of atmospheric to about 100 atmospheres, a hydrogen to hydrocarbon mole ratio of about 0.5:1 to about 20:1, and an LHSV (calculated on the basis of equivalent liquid volume of the charge stock contacted with the catalyst per hour divided by the volume of conversion zone containing catalyst) of about 0.2 hr.$^{-1}$ to 10 hr.$^{-1}$. Dehydrogenation conditions include: a temperature of about 700° to about 1250° F., a pressure of about 0.1 to about 10 atmospheres, a liquid hourly space velocity of about 1 to 40 hr.$^{-1}$, and a hydrogen to hydrocarbon mole ratio of about 1:1 to 20:1. Likewise, typically hydrocracking conditions include: a pressure of about 500 psig. to about 3000 psig., a temperature of about 400° F. to about 900° F., an LHSV of about 0.1 hr.$^{-1}$ to about 10 hr.$^{-1}$, and hydrogen circulation rates of about 1000 to 10,000 SCF per barrel of charge.

In the reforming embodiment of the present invention, the pressure utilized is selected from the range of about 0 psig. to about 1000 psig., with the preferred pressure being about 50 psig. to about 600 psig. Particularly good results are obtained at low or moderate pressure; namely, a pressure of about 100 to 450 psig. In fact, it is a singular advantage of the present invention that it allows stable operation at lower pressure than have heretofore been successfully utilized in so-called "continuous" reforming systems (i.e. reforming for periods of about 15 to about 200 or more barrels of charge per pound of catalyst without regeneration) with all platinum monometallic catalyst. In other words, the acidic sulfur-free multimetallic catalyst of the present invention allows the operation of a continuous reforming system to be conducted at lower pressure (i.e. 100 to about 350 psig) for about the same or better catalyst cycle life before regeneration as has been heretofore realized with conventional monometallic catalysts at higher pressure (i.e. 400 to 600 psig). On the other hand, the extraordinary activity and activity-stability characteristics of the catalyst of the present invention enables reforming conditions conducted at pressures of 400 to 600 psig. to achieve substantially increased catalyst cycle life before regeneration.

The temperature required for reforming with the instant catalyst is markedly lower than that required for a similar reforming operation using a high quality catalyst of the prior art. This significant and desirable feature of the present invention is a consequence of the extraordinary activity of the acidic sulfur-free multimetallic catalyst of the present invention for the octane-upgrading reactions that are preferably induced in a typical reforming operation. Hence, the present invention requires a temperature in the range of from 800° F. to about 1100° F. and preferably about 900° F. to about 1050° F. As is well known to those skilled in the continuous reforming art, the initial selection of the temperature within this broad range is made primarily as a function of the desired octane of the product reformate considering the characteristics of the charge stock and of the catalyst. Ordinarily, the temperature then is thereafter slowly increased during the run to compensate for the inevitable deactivation that occurs to provide a constant octane product. Therefore, it is a feature of the present invention that not only is the initial temperature requirement substantially lower, but also the rate at which the temperature is increased in order to maintain a constant octane product is substantially lower for the catalyst of the present invention than for an equivalent operation with a high quality reforming catalyst which is manufactured in exactly the same manner as the catalyst of the present invention except for the inclusion of the cobalt and rhenium components. Moreover, for the catalyst of the present invention, the $C_5+$ yield loss for a given temperature increase is substantially lower than for a high quality reforming catalyst of the prior art. The extraordinary activity of the instant catalyst can be utilized in a number of highly beneficial ways to enable increased performance of a catalytic reforming process relative to that obtained in a similar operation with a monometallic or bimetallic catalyst of the prior art, some of these are: (1) Octane number of $C_5+$ product can be substantially increased without sacrificing catalyst run length. (2) The duration of the process operation (i.e. catalyst run length or cycle life) before regeneration becomes necessary can be significantly increased. (3) Investment costs can be lowered without any sacrifice in cycle life by lowering recycle gas requirements thereby saving on capital cost for compressor capacity or by lowering initial catalyt loading requirements thereby saving on cost of catalyst and on capital cost of the reactors. (4) Througput can be increased at no sacrifice in catalyst cycle life if sufficient heater capacity is available.

The reforming embodiment of the present invention also typically utilizes sufficient hydrogen to provide an amount of about 1 to about 20 moles of hydrogen per mole of hydrogen entering the reforming zone, with excellent results being obtained when about 2 to about 6 moles of hydrogen are used per mole of hydrocarbon. Likewise, the liquid hourly space velocity (LHSV) used in reforming is selected from the range of about 0.1 to about 10 hr.$^{-1}$, with a value in the range of about 1 to about 5 hr.$^{-1}$ being preferred. In fact, it is a feature of the present invention that it allows operations to be conducted at higher LHSV than normally can be stably achieved in a continuous reforming process with a high quality reforming catalyst of the prior art. This last feature is of immense economic significance because it allows a continuous reforming process to operate at the same throughput level with less catalyst inventory or at greatly increased throughput level with the same catalyst inventory than that heretofore used with conventional reforming catalysts at no sacrifice in catalyst life before regeneration.

It is intended to cover by the following claims all changes and modifications of the above disclosure of the present invention which would be self-evident to a man of ordinary skill in the catalyst formulation art or the hydrocarbon conversion art.

I claim as my invention:

1. A process for converting a hydrocarbon which comprises contacting the hydrocarbon at hydrocarbon coversion conditions with an acidic sulfur-free catalytic composite comprising a porous carrier material containing, on an elemental basis, about 0.01 to about 2 wt.% platinum group metal, about 0.1 to about 5 wt.% cobalt, about 0.01 to about 2 wt.% rhenium, and about 0.1 to about 3.5 wt.% halogen; wherein the platinum group metal, catalytically available cobalt, and rhenium are uniformly dispersed throughout the porous material; wherein substantially all of the platinum group metal is present in the elemental metallic state; and wherein substantially all of the rhenium and catalytically available cobalt are present in the elemental metallic state or in state which is reducible to the elemental metallic state under hydrocarbon conversion conditions or in a mixture of these states.

2. A process as defined in claim 1 wherein the platinum group metal is platinum.

3. A process as defined in claim 1 wherein the platinum group metal is iridium.

4. A process as defined in claim 1 wherein the platinum group metal is rhodium.

5. A process as defined in claim 1 wherein the platinum group metal is palladium.

6. A process as defined in claim 1 wherein the porour carrier material is a refractory inorganic oxide.

7. A process as defined in claim 6 wherein the refractory inorganic oxide is alumina.

8. A proces as defined in claim 1 wherein the porous carrier material contains catalytically unavailable cobalt.

9. A process as defined in claim 8 wherein the catalytically unavailable cobalt is combined with the carrier material in the form of a refractory cobalt oxide or aluminate.

10. A process as defined in claim 1 wherein the catalytically available cobalt comprises at least about 10% of the total cobalt content of the catalytic composite.

11. A process as defined in claim 1 wherein the halogen is combined chloride.

12. A process as defined in claim 1 wherein the atomic ratio of rhenium to platinum group metal contained in the composite is about 0.05:1 to about 10:1.

13. A process as defined in claim 1 whereinte atomic ratio of cobalt to platinum group metal combined in the composite is about 0.2:1 to about 66:1.

14. A process as defined in claim 1 wherein substantially all of the catalytically available cobalt contained in the composite is present in the elemental metallic state after the process is started-up and lined-out at hydrocarbon conversion conditions.

15. A process as defined in claim 1 wherein the composite contains about 0.05 to about 1 wt.% platinum, about 0.25 to about 2.5 wt.% cobalt, about 0.05 to about 1 wt.% rhenium, and about 0.5 to about 1.5 wt.% halogen.

16. A process as defined in claim 1 wherein the contacting of the hydrocarbon with the catalytic composite is performed in the presence of hydrogen.

17. A process as defined in claim 1 wherein the type of hydrocarbon conversion is catalytic reforming of a gasoline fraction to produce a high octane reformate, wherein the hydrocarbn is contained in the gasoline fraction, wherein the contacting is performed in the presence of hydrogen, and wherein the hydrocarbon conversion conditions are reforming conditions.

18. A process as defined in claim 17 wherein the reforming conditions include a temperature of about 800° to about 1100° F., a pressure of about 0 to about 1000 psig., a liquid hourly space velocity of about 0.1 to about 10 hr.$^{-1}$, and a mole ratio of hydrogen to hydrocarbon of about 1:1 to about 20:1.

19. A process as defined in claim 17 wherein the contacting is performed in a substantially water-free environment.

20. A process as defined in claim 17 wherein the reforming conditions includes a pressure of about 100 to about 450 psig.

21. A process as defined in claim 17 wherein the contacting is performed in a substantially sulfur-free environment.

22. A process as defined in claim 15 wherein the type of hydrocarbon conversion is catalytic reforming of a gasoline fraction to produce a high octane reformate, wherein the hydrocarbon is contained in the gasoline fraction, wherein the contacting is performed in the presence of hydrogen, and wherein the hydrocarbon conversion conditions are reformig conditions.

23. An acidic sulfur-free catalytic composite comprising a porous carrier material containing, on an elemental basis, about 0.01 to about 2 wt% platinum group metal, about 0.1 to about 5 wt.% cobalt, about 0.01 to about 2 wt.% rhenium, and about 0.1 to about 3.5 wt.% halogen; wherein the platinum group metal, catalytically available cobalt, and rhenium are uniformly dispersed throughout the porous carrier material; wherein substantially all of the platinum group metal is present in the elemental metallic state; and wherein substantially all of the rhenium and catalytically available cobalt are present in the elemental metallic state or in a state which is reducible to the elemental metallic state under hydrocarbon conversion conditions or in a mixture of these states.

24. A catalytic composite as defined in claim 23 wherein the porous carrier metal contains catalytically unavailable cobalt.

25. A catalytic composiste as defined in claim 24 wherein the catalytically unavailable cobalt is combined with the carrier material in the form of a refractory cobalt oxide or aluminate.

26. A catalytic composite as defined in claim 23 wherein the catalytically available cobalt comprises at least about 10% of the total cobalt content of the catalytic composite.

* * * * *